United States Patent [19]

Biedermann et al.

[11] Patent Number: 5,964,762
[45] Date of Patent: Oct. 12, 1999

[54] BONE PLATE

[76] Inventors: Lutz Biedermann, Am Schäfersteig 8, 78048 VS-Villingen, Germany, 78048; Jürgen Harms, Vogesenstrasse 60, 76337 Waldbronn, Germany, 76337

[21] Appl. No.: 09/068,325
[22] PCT Filed: Sep. 15, 1997
[86] PCT No.: PCT/EP97/05048
§ 371 Date: May 5, 1998
§ 102(e) Date: May 5, 1998
[87] PCT Pub. No.: WO98/11837
PCT Pub. Date: Mar. 26, 1998
[51] Int. Cl.⁶ .......................... A61B 17/56; A61B 17/58; A61F 2/30
[52] U.S. Cl. ................................ 606/69; 606/61
[58] Field of Search ................. 606/69, 60, 72, 606/61

[56] References Cited

U.S. PATENT DOCUMENTS

| 3,604,414 | 9/1971 | Borges et al. ............ 128/92 D |
| 3,659,595 | 5/1972 | Haboush .................. 128/92 D |

FOREIGN PATENT DOCUMENTS

| 1 239 266 | 7/1960 | France . |
| 2 689 750 | 11/1993 | France . |
| 28 08 971 A1 | 9/1979 | Germany . |
| 86 24 671.2 U1 | 12/1986 | Germany . |
| 40 07 306 C1 | 5/1991 | Germany . |
| 627580 | 8/1949 | United Kingdom . |
| WO 96/01298 | 2/1996 | WIPO . |

*Primary Examiner*—Michael Buiz
*Assistant Examiner*—Vy Q. Bui
*Attorney, Agent, or Firm*—Dike, Bronstein, Roberts & Cushman, LLP; George W. Neuner

[57] ABSTRACT

A bone plate having an elongated intermediate portion and at least a hole at each end for receiving an anchoring screw 10 is created. The bone plate should be usable for different lengths and should allow the possibility of contraction and distraction of parts to be connected during the operation in a simple manner. For this purpose, the intermediate portion comprises a first portion 1 having an elongated hole 3, 4 extending in the longitudinal direction of the intermediate portion and a second portion 2 having bores 13, 14 and being connectable with the first portion 1. A screw connecting the two portions is provided being guided through the elongated hole 3, 4 for connecting the two portions. One of the portions comprises a structured surface 18, and the other portion comprises a recess for registering therewith. Further, a fixing element 19 is provided for engagement with the structure for locking the relative position of the two portions 1, 2 relative to each other.

5 Claims, 2 Drawing Sheets

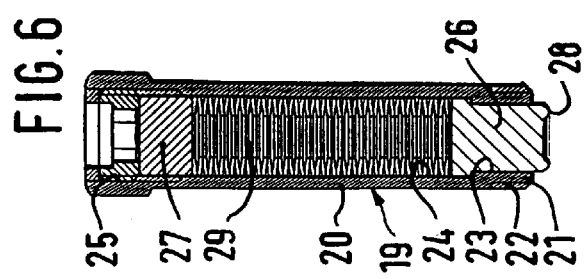
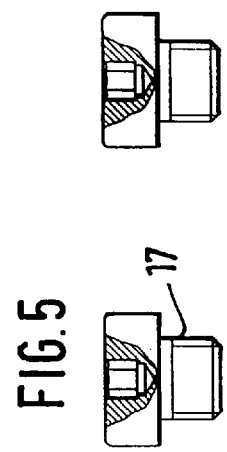
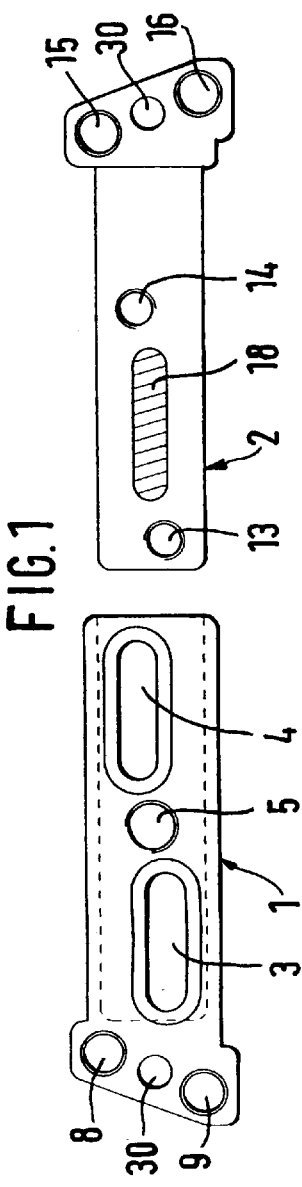
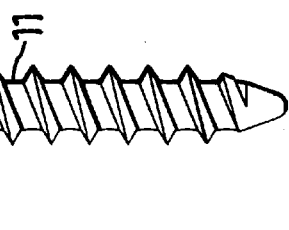
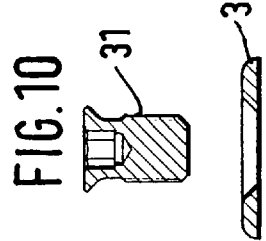
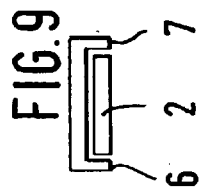
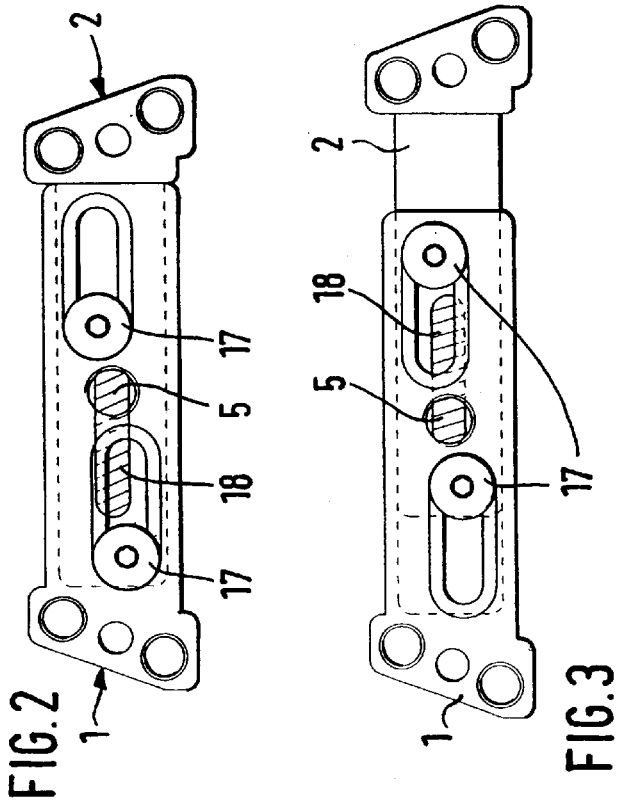

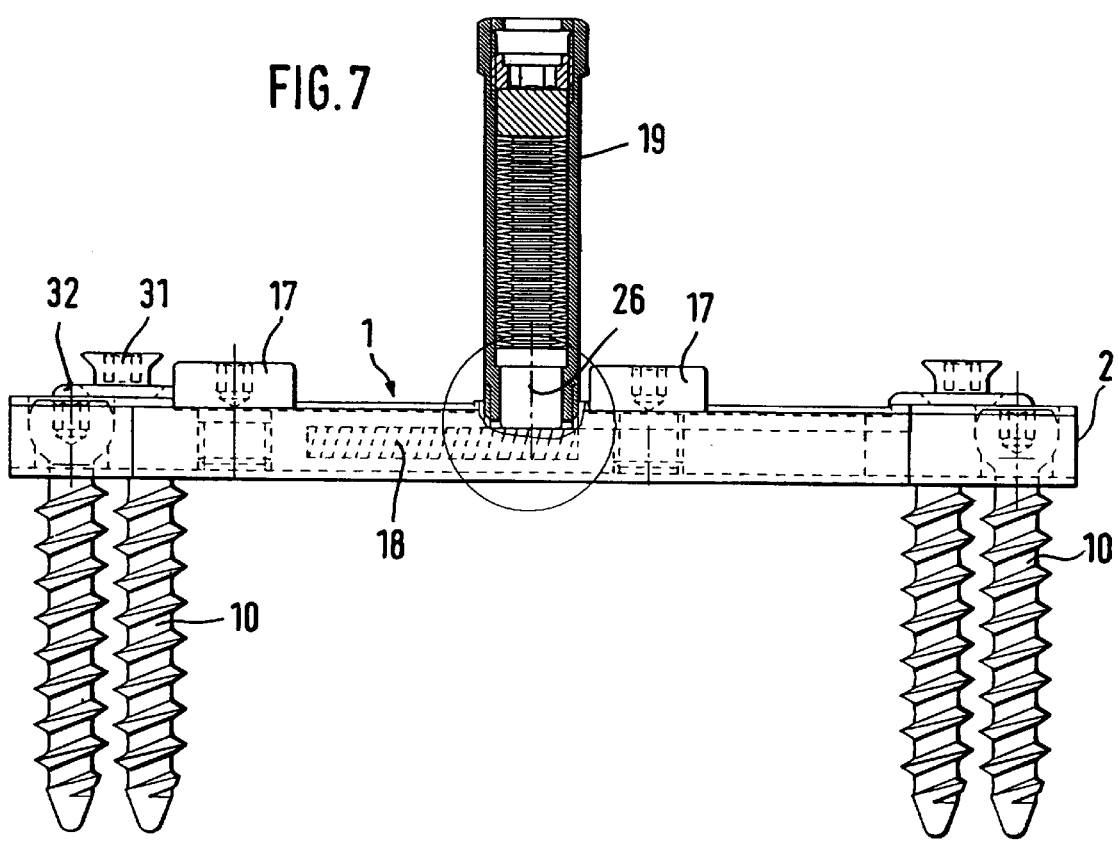
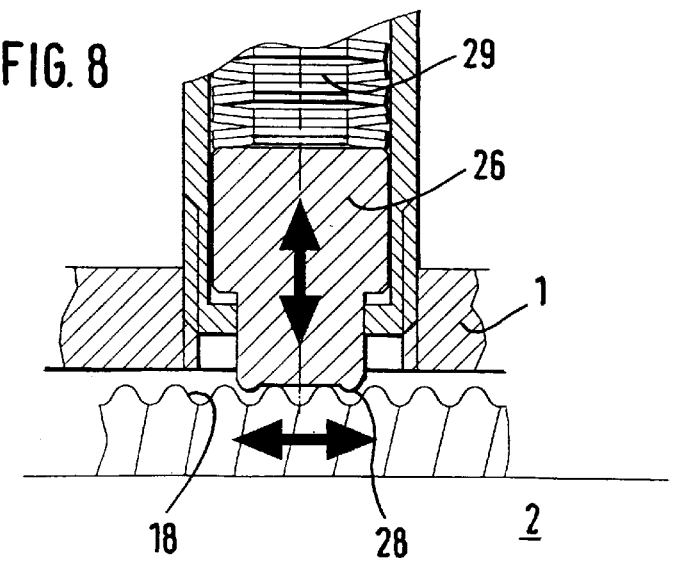

BONE PLATE

The invention relates to a bone plate comprising an intermediate portion with first and second ends, having at least a hole at each end for receiving an anchoring screw.

Bone plates are employed in particular in surgery of the vertebral column. To this purpose, different lengths of the bone plates are needed with different distances of the corresponding bone screws. The surgeon has a supply of a set of different sizes of such plates for this purpose. Already this store-keeping is disadvantageous. Furthermore, often the operation requires an adjustment of the parts to be connected with each other so that during an operation successively plates of different lengths have to be applied.

It is the object of the invention to provide a bone plate which removes the disadvantages described above.

According to the invention, a bone plate is provided, comprising an elongated intermediate portion with first and second ends, having at least a hole at each end for receiving an anchoring screw, said intermediate portion comprising a first portion having an elongated hole extending in the longitudinal direction of said intermediate portion, a second portion connectable with said first portion and having a bore, a screw connecting said two portions and being guided through said elongated hole, a surface portion comprising a structured surface at said second portion of said intermediate portion and a recess for registering with said structured surface in said first portion, and a fixing element for engaging with said surface portion for the purpose of locking the relative position of said first and second portions with respect to each other.

Preferably, the recess is formed as a threaded bore for receiving said fixing element.

Preferably, the fixing element has a longitudinal direction and comprises an element resiliently biased in the longitudinal direction against a rod for biasing the rod towards the structured surface on the first portion.

Preferably, the structured surface comprises a screw-shaped waviness.

Preferably, the rod biased to the structured surface comprises an annular projection for engagement with the structured surface.

In the inventive bone plate, the disadvantageous store-keeping is not only eliminated but it is also possible, by varying the relative position of the two portions with each other, to carry out a distraction or contraction, respectively, of the portions to be connected and to carry out a preliminary locking without loosening the anchoring screws nor without replacing the bone plates.

Further features and advantages will be apparent from the description of an embodiment with reference to the figures.

The figures show:

FIG. 1 a plan view of the detached two portions of the bone plate;

FIG. 2 the bone plate adjusted to the minimal length;

FIG. 3 the same bone plate adjusted to the maximum length;

FIG. 4 a side view of an anchoring screw;

FIG. 5 a side view of a locking screw;

FIG. 6 a sectional view through a fixing element;

FIG. 7 a side view of the bone plate with inserted anchoring screws and fixing element on an enlarged scale;

FIG. 8 a detailed illustration of FIG. 7 in a further enlarged scale;

FIG. 9 a section through the bone plate; and

FIG. 10 a section through a securing element.

The bone plate is described referring to FIG. 1 to 3 initially.

The bone plate comprises a first portion 1 and a second portion 2. The first portion 1 has the shape of an elongated rectangular plate with a first elongated hole 3 extending in parallel to the longitudinal axis and offset from the center to a side edge. Further, a corresponding second elongated hole 4 is provided extending in parallel to the first elongated hole 3 and offset from the center to the opposite side edge of the plate. A threaded bore 5 is provided between the two elongated holes 3, 4. As can be seen in FIG. 9, the two edges 6, 7 are formed on the lower surface of the plate extending downwards such that the second portion 2 is guided between the lower surface of the plate and the side edges 6, 7 in the manner of a rail. At one end, the first portion comprises two bores 8, 9 offset from the center for receiving the anchoring screws 10 shown in FIG. 4. The bores are spherically countersunk in a known manner so that the anchoring screws are arranged with the spherically shaped portion of the side of the head 12 facing the shaft 11 in the countersunk portion and are pivotable by a predetermined angle.

The second portion is also shaped as an elongated rectangle, its outer dimensions being selected such that it is slidable in the above-described rail-shaped lower surface of the first portion. In particular, the width of the plate-shaped portion is slightly smaller than the distances of the edges 6, 7 from each other, and the length corresponds essentially to the length of the rail-shaped portion. The second portion comprises a first threaded bore 13 being offset to the first edge by a predetermined amount from the symmetry axis of the plate such that the center point of the threaded bore 13 coincides with the center axis of the first elongated hole 3 when the second portion is shifted into the first portion. Further, a second threaded bore 14 is provided being offset to the opposite side edge such that its center point coincides with the center axis of the second elongated hole 4 if both portions are shifted into each other. The arrangement of the two threaded bores 13, 14 in the longitudinal direction of the plate of the second portion is selected such that the two center points of the threaded bores 13, 14 coincide in the fully pushed-in condition shown in FIG. 2 with the center points of the semicircular edges of the elongated holes 3, 4 facing the corresponding bores 8, 9. At the ends opposite to the bores 8, 9 during pushing-in, the second portion comprises corresponding bores 15, 16 for receiving anchoring screws 10.

The two portions 1, 2 are connected with each other in that locking screws shown in FIG. 5 are screwed loosely into the threaded bores 13, 14 through the elongated holes 3, 4 from the side opposite to the second portion. In such a manner, a relative motion of the two portions is possible between the pushed-in position shown in FIG. 2 and the extended position shown in FIG. 3 wherein the locking screws 17 contact the other end of the elongated holes 3, 4.

As can be seen best in FIG. 1, the plate of the second portion 2 comprises a portion 18 having a structure between the two threaded bores 13 and 15. In the embodiment shown, the structure is formed in that a screw segment, as can be seen best in FIG. 7 and 8, is formed in parallel to the center axis extending in longitudinal direction, the surface of which comprising grooves extending in the circumferential direction of the screw-shaped portion, or which is formed in the manner of a thread or a knurling. The center axis of the structured portion extends in the pushed-in position through the center point of the threaded bore 5, as can be seen from FIG. 2 and 3. The length of the structured portion is at least equal to the length of the elongated holes 3, 4. Its position relative to the elongated holes 3, 4 is selected such that the threaded bore 5 always registers with the structured portion 18 from the pushed-in position shown in FIG. 2 to the maximum extended position shown in FIG. 3.

For adjusting the relative position of the two portions 1, 2 with respect to each other an adjusting tool 19 is provided as is shown in FIG. 6. A device of this type is known from WO96/02198. It comprises a case with a cylindrical casing 20 and a front face 21. In the region of the casing adjacent to the front face 21 an external thread 22 is provided corresponding to the internal thread of the threaded bore 5. In the front face of the casing a cylindrical bore 23 having a first radius is provided. Adjacent to the cylindrical portion 23 a coaxial bore 24 is provided in the interior of the case, the diameter of which being larger than the diameter of the cylindrical portion 23. The bore 24 extends to the end of the casing opposite to the front face so that the case is open at this end. At this end of the casing opposite to the front face the casing comprises an internal thread 25. Further, this end comprises a hexagon cross-section for engaging with a wrench. The adjusting tool 19 further comprises a pressure part 26 held in the case which slides in the cylindrical portion 23 and which comprises at its end opposite to the front face a diameter corresponding to the coaxial bore 24 forming an abutment for a maximum extension in the manner shown in FIG. 6. The length of the pressure part is formed such that in the abutment position shown in FIG. 6 the pressure part extends with its free end further than the front face 21 to the outside. On the side opposite to the extending free end of the pressure part a compression spring 29 engaging with its other end at a screw 27 screwed into the internal thread 25. The pressure part 26 comprises at its front face projecting from the opening of the case 20 an angular projection 28, the edges thereof being rounded. The diameter of the angular projection corresponds to an integer multiple of the pitch of the round thread of the structured portion 18, and the height of the angular projection is smaller than the pitch of the round thread so that corresponding opposite regions of the angular projection can engage into the thread turns of the structured portion 18 when the adjusting tool 19 is screwed into the threaded bore 5 in the manner shown in FIG. 7 or 8, respectively.

In each of the edge portions of the first and second portions comprising the bores 8, 9 and 15, 16, respectively, a threaded bore 30 is provided. It serves for receiving a securing screw 31 with associated securing plate 32 shown in FIG. 10. The arrangement of the threaded bore 30 relative to the bores 8, 9 and 15, 16, respectively, is selected such that the securing plate just extends over the side edge of the anchoring screw 10 when the anchoring screws 10 are inserted, but without covering the concentrical hexagon bore 33 in the head of the anchoring screw 10 serving for engagement with a wrench tool.

During operation, the surgeon adjusts the approximate length of the bone plate by pulling out or pushing in the second portion from or into the first portion, respectively, and he adjusts this position by means of the adjusting tool inserted into the bore 5. Thereafter, he sets the anchoring screws 10. Subsequently, a distraction or contraction takes place by shifting the two portions 1, 2 under the effect of the adjusting tool relatively to each other. When the final ajdustment is obtained, firstly only the loosely screwed locking screws 17 are locked. The loosening and replacing of the anchoring screws 10 and the replacement of the plates, which were necessary up to now, is omitted. At the end, the adjusting tool is removed and the securing screws 31 are tightened.

We claim:

1. A bone plate comprising:

an elongated intermediate portion comprising a first end and a second end, and having at least a hole at each end for receiving an anchoring screw, said intermediate portion comprising a first portion and a second portion, said first portion having an elongated hole extending in a longitudinal direction of said intermediate portion, said second portion connectable with said first portion and having a bore, a screw connecting said first and second portions and being guided through said elongated hole, a surface portion comprising a structured surface at said second portion of said intermediate portion and a recess for registering with said surface portion in said first portion, and a fixing element for engaging with said surface portion for the purpose of adjusting the relative locking position of said first and second portions with respect to each other.

2. The bone plate according to claim 1, wherein said recess is formed as a threaded bore for receiving said fixing element.

3. The bone plate according to claim 2, wherein said fixing element has a longitudinal direction and comprises a rod and an element resiliently biased in the longitudinal direction against the rod for biasing the rod towards the structured surface on the first portion.

4. The bone plate according to claim 3, wherein said structured surface comprises a screw-shaped waviness.

5. The bone plate according to claim 4, wherein said rod that is biased to the structured surface comprises an annular projection for engagement with the structured surface.

* * * * *

UNITED STATES PATENT AND TRADEMARK OFFICE
CERTIFICATE OF CORRECTION

PATENT NO. : 5,964,762
DATED : October 12, 1999
INVENTOR(S) : Lutz Biedermann and Jurgen Harms It is certified that error appears in the above-identified patent and that said Letters Patent is hereby corrected as shown below:

Title page, item [30]

In the Foreign Patent Documents section, please add the priority data as follows:

[56] FOREIGN PATENT DOCUMENTS

GERMANY, SEPTEMBER 17, 1996, 196 37 938.5

Signed and Sealed this

Sixth Day of June, 2000

Attest:

Q. TODD DICKINSON

*Attesting Officer*  *Director of Patents and Trademarks*